United States Patent
Asaoka et al.

(10) Patent No.: US 9,955,956 B2
(45) Date of Patent: May 1, 2018

(54) NEEDLE TUBE

(71) Applicant: OLYMPUS CORPORATION, Hachioji-shi, Tokyo (JP)

(72) Inventors: Nobuyoshi Asaoka, Tokyo (JP); Junichi Muramatsu, Sagamihara (JP); Keita Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 8 days.

(21) Appl. No.: 15/238,560

(22) Filed: Aug. 16, 2016

(65) Prior Publication Data

US 2016/0354066 A1 Dec. 8, 2016

Related U.S. Application Data

(63) Continuation of application No. PCT/JP2015/073376, filed on Aug. 20, 2015.

(30) Foreign Application Priority Data

Aug. 20, 2014 (JP) .................................. 2014-167864

(51) Int. Cl.
*A61B 10/02* (2006.01)
*A61B 10/04* (2006.01)
(Continued)

(52) U.S. Cl.
CPC ............ *A61B 10/0275* (2013.01); *A61B 1/05* (2013.01); *A61B 8/0841* (2013.01); *A61B 8/12* (2013.01);
(Continued)

(58) Field of Classification Search
CPC ............ A61B 10/0233; A61B 10/0266; A61B 10/0275; A61B 10/04; A61B 10/0241;
(Continued)

(56) References Cited

U.S. PATENT DOCUMENTS 3,007,471 A * 11/1961 McClure, Jr. ...... A61B 10/0266
600/567
3,683,892 A * 8/1972 Harris .................... A61B 10/02
30/113.1
(Continued)

FOREIGN PATENT DOCUMENTS

EP 0966920 A2 12/1999
JP H10-94601 A 4/1998
(Continued)

OTHER PUBLICATIONS

Oct. 27, 2015 International Search Report issued in International Patent Application No. PCT/JP2015/073376.
(Continued)

*Primary Examiner* — Adam J Eiseman
(74) *Attorney, Agent, or Firm* — Oliff PLC

(57) ABSTRACT

A needle tube includes: a tubular main body section; a distal opening section; a needle tip; a side hole disposed closer to the proximal end side of the main body than the tip; a side hole inner circumferential edge extending around the longitudinal axis of the main body where the side hole and the inner circumferential surface intersect; a side hole outer circumferential edge extending around the longitudinal axis of the main body where the side hole and the outer circumferential surface intersect; and an engaged surface formed between the side hole inner circumferential edge and the side hole outer circumferential edge to be directed toward the proximal end of the main body section and configured to lock biological tissue entering from the distal opening section, wherein the side hole forms an opening area smaller than that of the distal opening.

20 Claims, 13 Drawing Sheets

(51) Int. Cl.
*A61B 1/05* (2006.01)
*A61B 8/12* (2006.01)
*A61B 8/00* (2006.01)
*A61B 8/08* (2006.01)

(52) U.S. Cl.
CPC ............ *A61B 8/4416* (2013.01); *A61B 10/02* (2013.01); *A61B 10/04* (2013.01); *A61B 10/0283* (2013.01); *A61B 2010/045* (2013.01)

(58) Field of Classification Search
CPC .............. A61B 10/025; A61B 10/0258; A61B 17/32053; A61B 2017/0034
See application file for complete search history.

(56) References Cited

U.S. PATENT DOCUMENTS

| | | | | |
|---|---|---|---|---|
| 4,903,709 | A * | 2/1990 | Skinner | A61B 10/0266 600/567 |
| 5,928,162 | A * | 7/1999 | Giurtino | A61B 10/0266 600/567 |
| 6,346,095 | B1 * | 2/2002 | Gross | A61M 5/3291 604/272 |
| 7,201,722 | B2 * | 4/2007 | Krueger | A61B 10/025 600/564 |
| 7,914,463 | B2 * | 3/2011 | Tarter | A61B 10/0275 600/567 |
| D657,461 | S * | 4/2012 | Schembre | A61B 10/0275 D24/130 |
| 2003/0050574 | A1 | 3/2003 | Krueger | |
| 2005/0101879 | A1 * | 5/2005 | Shidham | A61B 10/0283 600/566 |
| 2006/0161192 | A1 * | 7/2006 | Young | A61B 17/3415 606/185 |
| 2011/0098596 | A1 * | 4/2011 | Ozturk | A61B 10/0275 600/566 |
| 2012/0165832 | A1 | 6/2012 | Oostman, Jr. et al. | |
| 2013/0237879 | A1 * | 9/2013 | Takeuchi | A61B 8/0841 600/567 |
| 2015/0230780 | A1 * | 8/2015 | Schembre | A61B 10/0275 600/458 |
| 2015/0342580 | A1 * | 12/2015 | Clancy | A61B 10/04 600/567 |

FOREIGN PATENT DOCUMENTS

| | | |
|---|---|---|
| JP | 2008-154842 A | 7/2008 |
| JP | 2008-528207 A | 7/2008 |
| JP | 2013-523333 A | 6/2013 |
| WO | 2006/081556 A2 | 8/2006 |
| WO | 2011/126963 A2 | 10/2011 |
| WO | WO 2012133276 A1 * 10/2012 ........... A61B 8/0841 |

OTHER PUBLICATIONS

Mar. 14, 2018 Search Report issued in European Patent Application No. 15833380.7.

* cited by examiner

NEEDLE TUBE

This application is a continuation application, based on PCT/JP2015/073376, filed on Aug. 20, 2015, claiming priority based on Japanese Patent Application No. 2014-167864, filed in Japan on Aug. 20, 2014, the content of which is incorporated herein by reference.

FIELD OF THE INVENTION

The present invention relates to a needle tube that is applied to a biopsy needle.

DESCRIPTION OF THE RELATED ART

A medical needle which is capable of inserting in a biological tissue is widely known (for example, see Japanese Unexamined Patent Application, First Publication No. 2008-154842, and Japanese Unexamined Patent Application, First Publication No. H10-94601). In addition, an inspection method that is referred to as a biopsy of collecting a small amount of body tissue and inspecting the body tissue is known. When tissue of a deep part of an organ or the like is collected in a biopsy, since observation by an optical endoscope becomes difficult, an ultrasonogram of the organ is acquired by an ultrasonic endoscope or the like, and a biopsy needle is inserted in the organ to collect the tissue under ultrasonic observation (for example, see Japanese Unexamined Patent Application Publication (Translation of PCT Application) No. 2013-523333).

The biopsy needle disclosed in Japanese Unexamined Patent Application Publication (Translation of PCT Application) No. 2013-523333 has a needle tube (cannula) that punctures the tissue, and the needle tube has an opening section formed in a sidewall portion of the needle tube to capture the tissue in the needle tube and a cavity configured to hold the tissue captured from the opening section in the needle tube.

SUMMARY OF THE INVENTION

Means for Solving the Problem

An aspect of the present invention is a needle tube applied to a biopsy needle used with an endoscope, the needle tube including: a tubular main body section having a distal end, a proximal end, an inner circumferential surface and an outer circumferential surface and having an internal space formed by the inner circumferential surface; a distal opening section formed at a distal end of the main body section to be inclined with respect to a longitudinal axis of the main body section and having a distal opening in communication with the internal space; a needle tip formed at a distal end of the distal opening section; a side hole disposed proximally to the needle tip and passing through the inner circumferential surface and the outer circumferential surface of the main body section; a side hole inner circumferential edge extending around the longitudinal axis of the main body section at a position at which the side hole and the inner circumferential surface of the main body section cross; a side hole outer circumferential edge extending around the longitudinal axis of the main body section at a position at which the side hole and the outer circumferential surface of the main body section cross; and an engaged surface formed between the side hole inner circumferential edge and the side hole outer circumferential edge to be directed toward the proximal end of the main body section and configured to lock biological tissue entering from the distal opening section, wherein the side hole forms an opening area smaller than that of the distal opening.

The needle tube of the aspect may further include: a distal inner circumferential edge formed to cross the distal opening section and the inner circumferential surface of the main body section; a distal outer circumferential edge that continues from the distal opening section and the outer circumferential surface of the main body section; and a blade surface formed between the inner circumferential edge and the outer circumferential edge to surround the distal opening.

In a cross section passing through a central axis of the main body section and the side hole and parallel to the longitudinal axis, the distal opening section may be inclined to form an angle ($\beta$) with respect to the longitudinal axis of the main body section; a straight line (L1) extending in a proximal end direction from a center of the distal opening toward an inner circumferential surface of a side at which the side hole is formed and forming the angle ($\beta$) with respect to the longitudinal axis may cross an intersection point (X) with the inner circumferential surface, and the engaged surface may be disposed distally to the intersection point (X).

In the cross section passing through a central axis of the main body section and the side hole and parallel to the longitudinal axis, a straight line (L2) parallel to the straight line (L1) and passing through a proximal end of the distal inner circumferential edge may cross an intersection point (Y) with the inner circumferential surface, and an opposite surface which faces to the engaged surface may be disposed distally to the intersection point (Y).

In a cross section passing through a central axis of the main body section and the side hole and parallel to the central axis, the engaged surface and the inner circumferential surface of the main body section may form an angle ($\alpha$), in a proximal end of the distal inner circumferential edge, the blade surface and the inner circumferential surface of the main body section may form the angle ($\beta$), and in a cross section passing through the side hole and perpendicular to the central axis, when at least one of an angle formed by a first cross-sectional portion, which extends along a central axis of the main body, of the side hole and the inner circumferential surface of the main body section and an angle formed by a second cross-sectional portion, which extends along the central axis of the main body, of the side hole and the inner circumferential surface of the main body section is an angle ($\gamma$), the angle ($\gamma$) may be larger than the angle ($\beta$) and smaller than the angle ($\alpha$).

In a cross section of the main body section perpendicular to a central axis of the main body section, an opening width of the side hole inner circumferential edge may be smaller than an inner diameter of the main body section, and an opening width of the side hole outer circumferential edge may be larger than the inner diameter of the main body section.

The side hole may further have an incision blade section disposed at a boundary portion between the inner circumferential surface of the main body section and the engaged surface along an inner circumference of the main body section and configured to dissect tissue captured in the main body section.

The engaged surface may be disposed at an opposite position of a proximal end of the blade surface inclined with respect to a centerline of the main body section with the centerline of the main body section interposed therebetween.

The engaged surface may be disposed at an opposite position of the proximal end of the distal inner circumferential edge with the centerline of the main body section interposed therebetween.

The engaged surface is a plane with respect to the inner circumferential surface of the main body section.

The distal opening section may have a sharp puncture blade section that is configured to enable the main body section to puncture the tissue in an entire periphery of the distal end of the main body section.

DETAILED DESCRIPTION OF THE INVENTION

Figure 1:
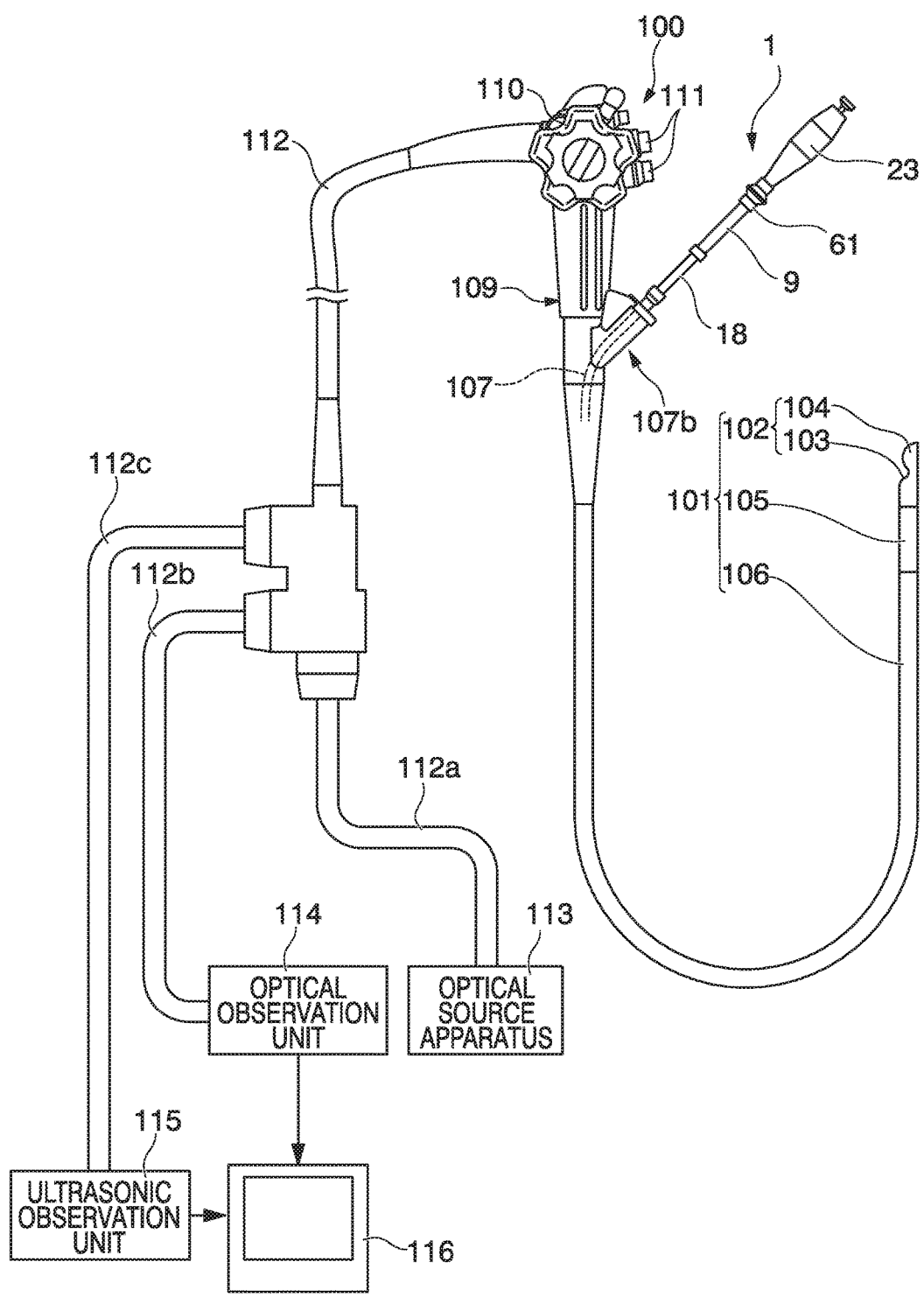
FIG. 1 is a general view showing a state in which a biopsy needle of an embodiment of the present invention is attached to an ultrasonic endoscope.
Figure 2:
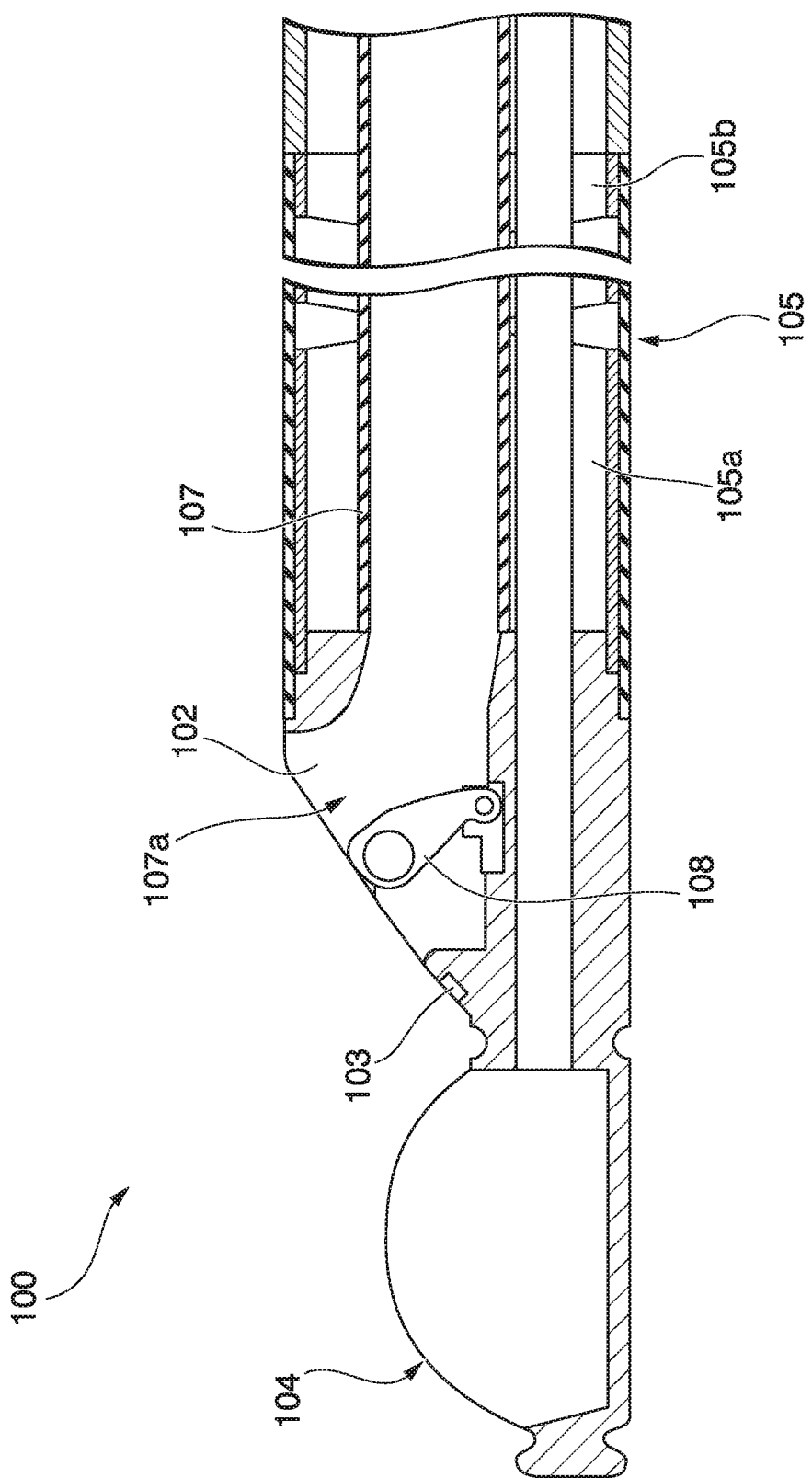
FIG. 2 is a cross-sectional view of a distal portion of the ultrasonic endoscope.
Figure 3:
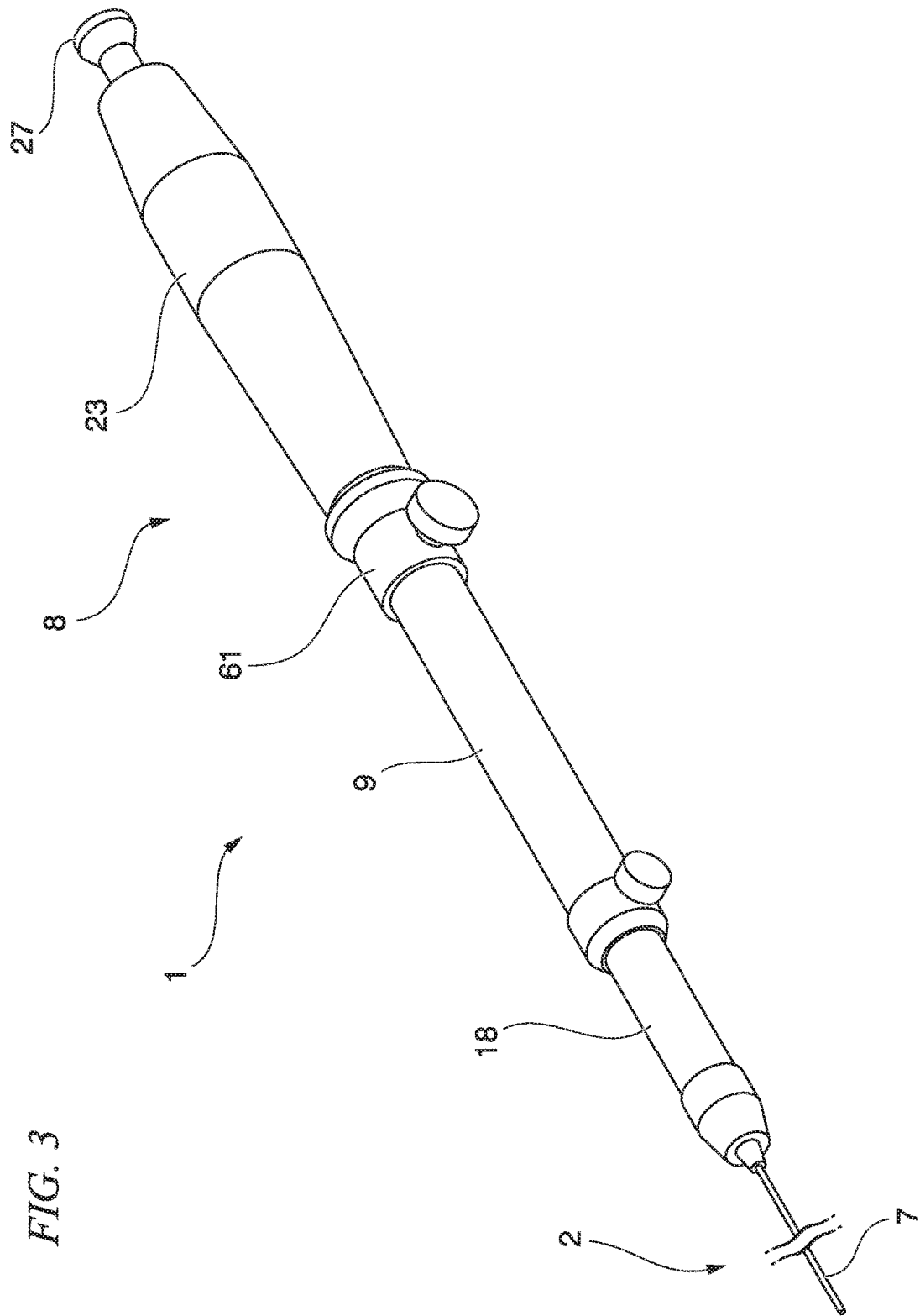
FIG. 3 is a perspective view of the biopsy needle.
Figure 4:
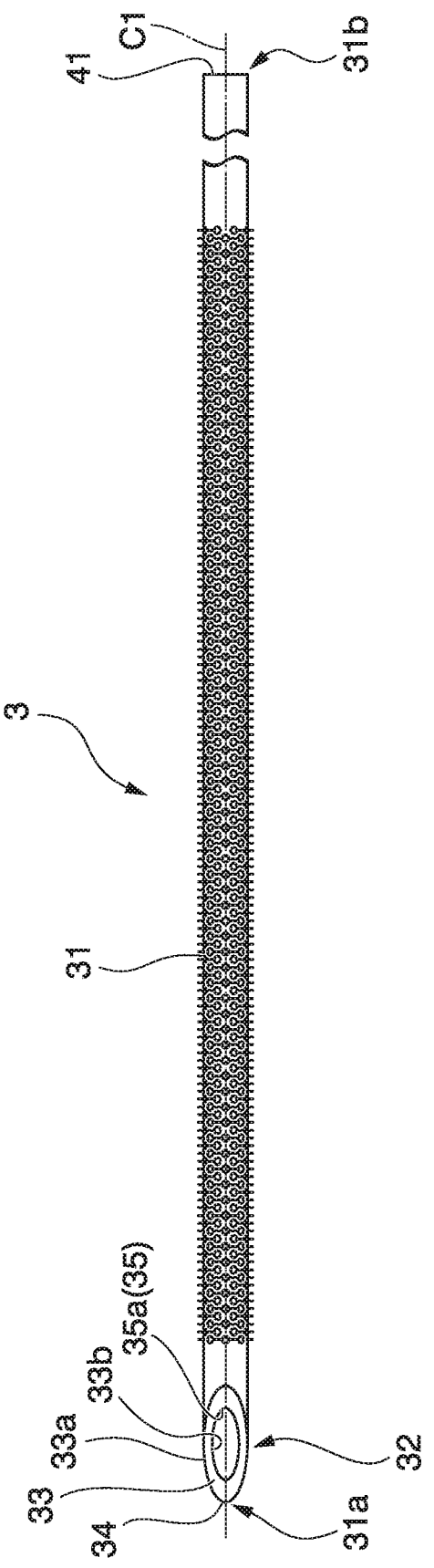
FIG. 4 is a plan view of a needle tube of the biopsy needle.
Figure 5:
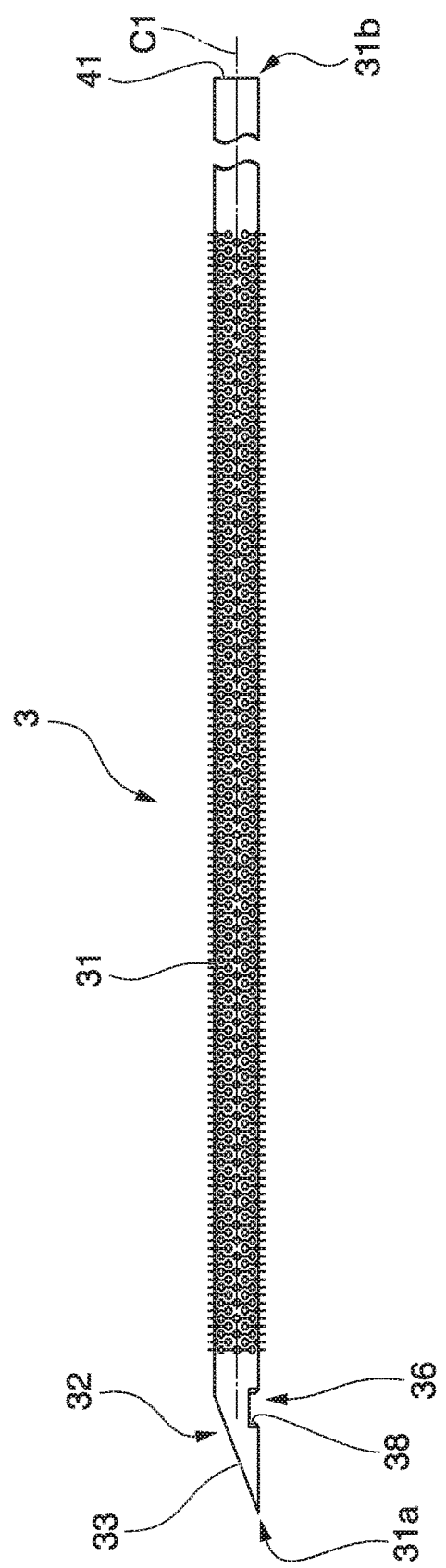
FIG. 5 is a side view of the needle tube of the biopsy needle.
Figure 6:
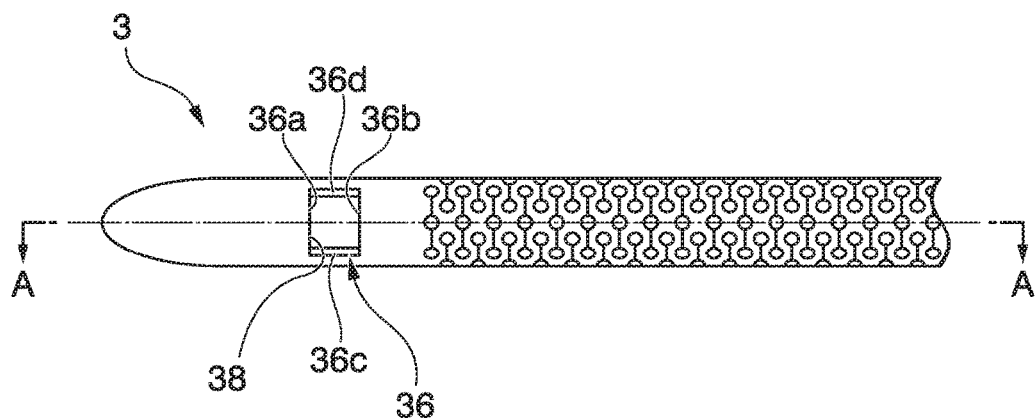
FIG. 6 is a bottom view of the needle tube of the biopsy needle.
Figure 7:
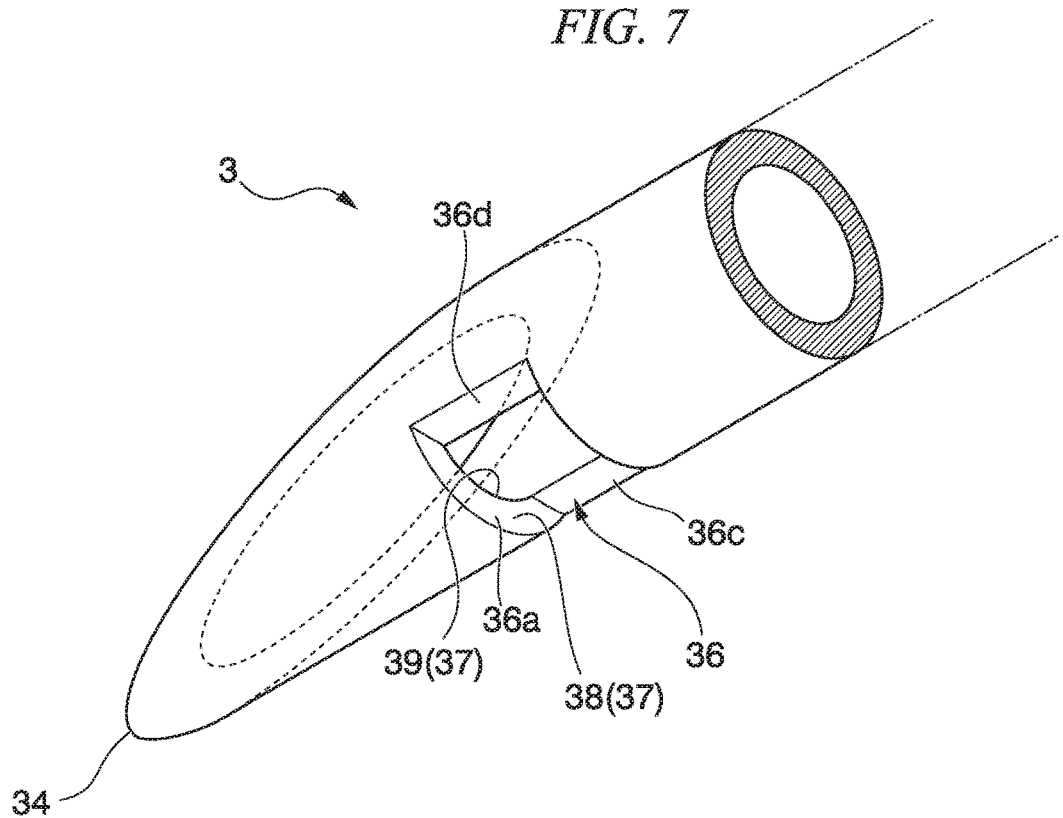
FIG. 7 is a perspective view of the distal portion of the needle tube of the biopsy needle.
Figure 8:
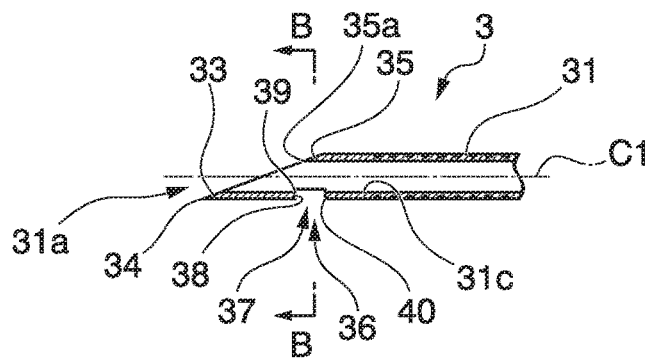
FIG. 8 is a cross-sectional view taken along line A-A of FIG. 6.
Figure 9:
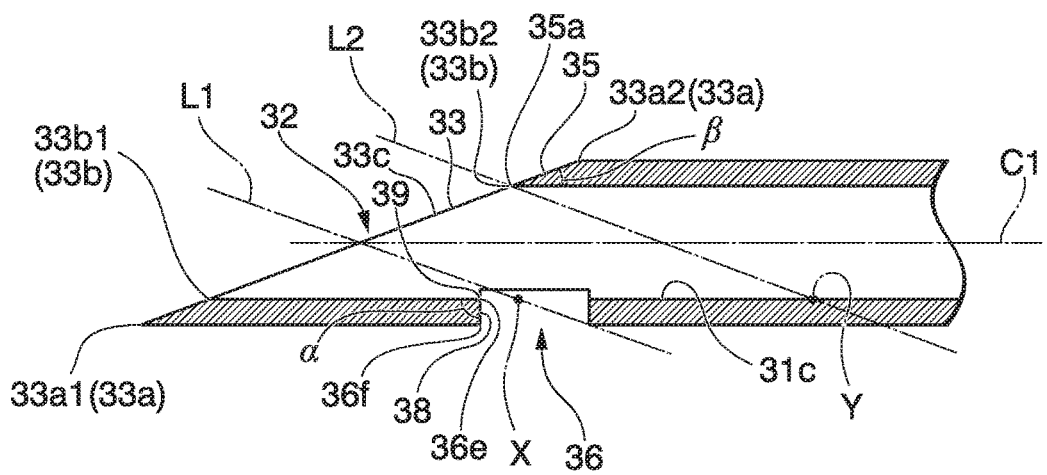
FIG. 9 is an enlarged view of FIG. 8.
Figure 10:
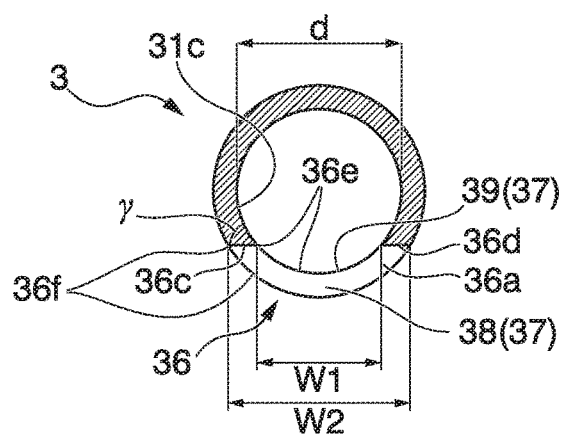
FIG. 10 is a cross-sectional view taken along line B-B of FIG. 8.

A biopsy needle including a needle tube of an embodiment of the present invention will be described. FIG. 1 is a general view showing a state in which the biopsy needle of the embodiment is attached to an ultrasonic endoscope. FIG. 2 is a cross-sectional view of a distal portion of an ultrasonic endoscope. FIG. 3 is a perspective view of the biopsy needle. FIG. 4 is a plan view of the needle tube of the biopsy needle. FIG. 5 is a side view of the needle tube of the biopsy needle. FIG. 6 is a bottom view of the needle tube of the biopsy needle. FIG. 7 is a perspective view of a distal portion of the needle tube of the biopsy needle. FIG. 8 is a cross-sectional view taken along line A-A of FIG. 6. FIG. 9 is an enlarged view of FIG. 8. FIG. 10 is a cross-sectional view taken along line B-B of FIG. 8.

As shown in FIG. 1, a biopsy needle 1 of the embodiment is an endoscopic medical instrument attached to an endoscope (for example, an ultrasonic endoscope 100) and is used therewith.

A configuration of the endoscope to which the biopsy needle 1 of the embodiment can be attached is not particularly limited. In the embodiment, the ultrasonic endoscope 100 capable of observing a tissue collecting area in a biopsy using ultrasonic waves is shown as an exemplary example.

The ultrasonic endoscope 100 shown in FIG. 1 includes an insertion section 101 inserted into a body from a distal end thereof, a manipulation section 109 attached to a proximal end of the insertion section 101, a universal cord 112 having a first end connected to a side portion of the manipulation section 109, a light source apparatus 113 connected to a second end of the universal cord 112 via a branch cable 112a, an optical observation unit 114 connected to the second end of the universal cord 112 via a branch cable 112b, and an ultrasonic observation unit 115 connected to the second end of the universal cord 112 via a branch cable 112c.

The insertion section 101 has a distal hard section 102, an active bending section 105 and a flexible tube section 106 that are formed sequentially from a distal side thereof.

As shown in FIGS. 1 and 2, the distal hard section 102 includes an optical imaging mechanism 103 configured to perform optical observation, an ultrasonic scanning mechanism 104 configured to perform ultrasonic observation, and a elevator 108 configured to adjust a direction of the biopsy needle 1 inserted through a channel 107, which will be described below.

The optical imaging mechanism 103 includes an imaging optical system in which a field of vision is directed toward an inclined forward side of the distal hard section 102, an image sensor such as a CCD, a CMOS, or the like, configured to detect an image of a subject that enters through the imaging optical system, and various constitutions (not shown) such as a CPU or the like configured to control an operation of the image sensor.

The ultrasonic scanning mechanism (probe) 104 includes an ultrasonic vibrator (not shown) configured to emit and receive ultrasonic waves. The ultrasonic scanning mechanism 104 receives reflected waves obtained when the ultrasonic waves emitted from the ultrasonic vibrator hit an observation target and are reflected using the ultrasonic vibrator, and outputs a signal to the ultrasonic observation unit 115 based on the ultrasonic waves received by the ultrasonic vibrator. The ultrasonic scanning mechanism 104 of the embodiment is used to acquire an ultrasonic wave image of the tissue serving as the biopsy target and acquire an ultrasonic wave image of a needle tube 3 in a process of a procedure of the biopsy.

The elevator 108 is a member configured to change a direction of a distal portion of a sheath 7 of the biopsy needle 1 into a direction crossing a centerline of the insertion section 101. The elevator 108 can press an outer surface of the sheath 7 and deform the sheath 7 into a curved state by pulling a raising wire (not shown) extending to the manipulation section 109 in the manipulation section 109.

The active bending section 105 is an active bending section which is capable of being curved in a predetermined direction by pulling an angle wire (not shown) fixed to a distal end 105a of the active bending section 105 and extending to the manipulation section 109 in the manipulation section 109. The active bending section 105 of the embodiment can be curved in two directions along a scanning direction of ultrasonic waves.

The flexible tube section 106 is a tubular member flexibly formed such that the distal hard section 102 in a lumen tissue or a body cavity can be guided to a predetermined position.

The channel 107 and a pipe line (not shown) configured to perform air supply and water supply, suction, or the like, are formed in the active bending section 105 and the flexible tube section 106, respectively.

The channel 107 is a tubular section through which the biopsy needle 1 can be inserted.

A first end of the channel 107 is opened in the vicinity of a distal portion of the distal hard section 102, and a second end of the channel 107 is opened at a side surface of a distal side of the manipulation section 109. In a process in which the sheath 7 of the biopsy needle 1 protrudes from the first end of the channel 107, the elevator 108 can come in contact with an outer surface of the sheath 7 of the biopsy needle 1. A proximal port member 107*b* formed in a flange shape is fixed to the second end of the channel 107. The biopsy needle 1 used with the ultrasonic endoscope 100 can be fixed to the proximal port member 107*b*.

The manipulation section 109 has an outer surface formed such that an operator who uses the ultrasonic endoscope 100 can hold the manipulation section with his/her hand. The manipulation section 109 includes a bending manipulation mechanism 110 configured to pull the angle wire to bend the active bending section 105 or pull the raising wire to operate the elevator 108, and a plurality of switches 111 configured to perform air supply, water supply or suction through the pipe line.

The light source apparatus 113 is an apparatus configured to emit illumination light for imaging using the optical imaging mechanism 103.

The optical observation unit 114 is configured to project pictures imaged by the image sensor of the optical imaging mechanism 103 on a monitor 116.

The ultrasonic observation unit 115 is configured to receive a signal output from the ultrasonic scanning mechanism 104 and generate the image based on the signal to project the image onto the monitor 116.

Further, the ultrasonic endoscope 100 including the above-mentioned configuration is an example of the endoscope that can be used with the biopsy needle 1 of the embodiment, and a configuration of the ultrasonic endoscope that can be attached to the biopsy needle 1 of the embodiment is not particularly limited. That is, the biopsy needle 1 of the embodiment can be appropriately applied to a known endoscope including a treatment tool channel.

Next, a configuration of the biopsy needle 1 of the embodiment will be described.

As shown in FIG. 3, the biopsy needle 1 includes an insertion body 2, a manipulation section 8 and a stylet 27.

The insertion body 2 is an elongated member that can be inserted through the channel 107 of the ultrasonic endoscope 100 shown in FIG. 1.

The insertion body 2 includes the needle tube 3 and the sheath 7.

The needle tube 3 shown in FIGS. 4 to 8 is disposed in the sheath 7 shown in FIG. 3. The needle tube 3 is a tubular member having a distal end and a proximal end and is manipulated by the manipulation section 8 of the biopsy needle 1 to advance and retreat. The material of the needle tube 3 may be a material having flexibility and elasticity such that the needle tube 3 can easily return to a straight state even when curved by an external force. For example, the material of the needle tube 3 may be an alloy material such as a stainless steel alloy, a nickel titanium alloy, a cobalt chromium alloy, or the like.

The needle tube 3 has a main body section 31 having a long tubular shape, a distal opening section 32 and a side hole 36 that are formed at a portion of a distal end 31*a* of the main body section 31, and a proximal end opening section 41 formed at a portion of a proximal end 31*b* of the main body section 31. The main body section 31 has a distal end, a proximal end, an inner circumferential surface 31*c* and an outer circumferential surface.

The distal opening section 32 is formed by diagonally cutting a distal end of a tubular member that forms the needle tube 3 off therefrom, and is formed sharply such that the distal opening section 32 can be inserted in the organ serving as the biopsy target.

In addition, in the main body section 31, an internal space formed by the inner circumferential surface 31*c* is provided, and a central axis (a centerline C1) passing through a center of the internal space is defined. The distal opening section 32 is formed at the distal end of the main body section 31 to be inclined with respect to a longitudinal axis of the main body section 31, and has an opening in communication with an internal space thereof. The distal opening of the distal opening section 32 is formed such that the tissue enters the internal space while puncture of the tissue is performed, and the distal opening has a predetermined opening area (first opening area). A specific shape of the distal opening section 32 may be appropriately selected from various kinds of known shapes in consideration of the tissue or the like serving as a target.

As shown in FIGS. 4 and 9, the needle tube 3 has a distal inner circumferential edge 33*b* that continues to the inner circumferential surface 31*c* of the needle tube 3 and the distal opening section 32, and a distal outer circumferential edge 33*a* that continues to the outer circumferential surface of the needle tube 3 and the distal opening section 32. Further, the needle tube 3 has a (tapered) blade surface 35 formed between the distal inner circumferential edge 33*b* and the distal outer circumferential edge 33*a* to surround the distal opening and inclined with respect to the centerline C1 of the main body section 31. The distal inner circumferential edge 33*b* of the distal opening section 32 defines an inlet configured to capture the tissue in the main body section 31. In the blade surface 35, a bottommost end 33*b*2 disposed at a lowermost proximal end on the distal inner circumferential edge 33*b* is a sharp-edged dissection blade section 35*a* configured to dissect the tissue and guide the tissue into the main body section 31 in the process of inserting the main body section 31 in the tissue. In the dissection blade section 35*a*, the inner circumferential surface 31*c* of the main body section 31 and the blade surface 35 form a first angle β (for example, 5 to 25°). In the blade surface 35, the distal outer circumferential edge 33*a* of the distal opening section 32 is an puncture blade section (a needle tip) 34 that is particularly sharp at a foremost distal end 33*a*1 at a most distal portion of the distal outer circumferential edge 33*a* and configured to dissect the tissue when the main body section 31 is inserted in the tissue.

As shown in FIGS. 5 to 8, the side hole 36 is a through-hole having an opening formed closer to a proximal end of the main body section 31 than the needle tip 34 and having a substantially rectangular shape in communication with (passing through) the inner circumferential surface 31*c* and the outer circumferential surface of the main body section 31. In addition, the side hole 36 is formed closer to the proximal end side than the foremost distal end 33*a*1 of the distal outer circumferential edge 33a of the distal opening section 32 and disposed at a position of the distal region of the main body section 31. An opening area (a second opening area) of the side hole 36 may be equal to or smaller than that of the distal opening section 32 of the needle tube 3. In this case, the tissue cannot easily enter the main body section 31 via the side hole 36, and the tissue can easily enter the needle tube from the distal opening section 32. In addition, the side hole 36 is an opening having a substantially rectangular shape in which a direction parallel to a longitudinal axis of the main body section 31 is a short side and a direction crossing the longitudinal axis of the main body section 31 is a long side. Further, an opening width (a first opening width) W1 of the side hole 36 on the inner circumferential surface 31c of the main body section 31 of the needle tube 3 is smaller than an inner diameter d of the inner circumferential surface 31c of the main body section 31. For this reason, the tissue cannot easily exit the side hole 36, and the tissue can easily stay in the needle tube 3. In addition, an opening width (a second opening width) W2 of the side hole 36 on the outer circumferential surface of the main body section 31 is larger than the inner diameter d of the needle tube 3. For this reason, the tissue entering the needle tube 3 can be sufficiently locked therein. Further, in the embodiment, while the opening of the side hole 36 is exemplified as having a substantially rectangular shape, a shape of the opening of the side hole 36 is not limited to the substantially rectangular shape and the shape of the opening may be a circular shape.

As shown in FIGS. 6 and 7, the side hole 36 is formed to be surrounded by cross-sectional portions 36a, 36b, 36c and 36d having a predetermined thickness, and the cross-sectional portions 36a, 36b, 36c and 36d form a side hole opening end serving as a surface (an edge surface) that forms a circumferential edge of the side hole 36. The cross-sectional portion 36a is a surface disposed at a distal side of the main body section 31, and the cross-sectional portion 36b is a surface disposed at a proximal side of the main body section 31 (a surface opposite to the cross-sectional portion 36a). The cross-sectional portion 36c (a first cross-sectional portion) and the cross-sectional portion 36d (a second cross-sectional portion) extend along a central axis of the main body section 31 between the cross-sectional portion 36a and the cross-sectional portion 36b, and are formed as surfaces directed in a substantially circumferential direction.

As shown in FIGS. 9 and 10, a second angle γ formed by the cross-sectional portion 36c (the cross-sectional portion 36d) and the inner circumferential surface 31c of the main body section 31 is larger than a first angle β, and the second angle γ may be, for example, within a range of 30 to 75°.

In addition, as shown in FIGS. 9 and 10, a side hole inner circumferential edge 36e extends around a longitudinal axis of the main body section 31 at a position at which the side hole 36 and the inner circumferential surface 31c of the main body section 31 intersect each other. Further, a side hole outer circumferential edge 36f extends around the longitudinal axis of the main body section 31 at a position at which the side hole 36 and the outer circumferential surface of the main body section 31 intersect each other.

Further, the above-mentioned opening width W1 is defined by a length from a boundary line between the cross-sectional portion 36c and the inner circumferential surface 31c to a boundary line between the cross-sectional portion 36d and the inner circumferential surface. The above-mentioned opening width W2 is defined by a length from a boundary line between the cross-sectional portion 36c and the outer circumferential surface of the main body section 31 to a boundary line between the cross-sectional portion 36d and the outer circumferential surface of the main body section 31.

The cross-sectional portion 36a is an engaged surface 38 configured to lock the tissue in the main body section 31. The engaged surface 38 is formed toward a proximal end of the main body section 31 between the side hole inner circumferential edge 36e and the side hole outer circumferential edge 36f. In addition, the boundary portion between the inner surface of the main body section 31 and the engaged surface 38 is an incision blade section 39 that can form an incision in the tissue from which the tissue in the needle tube is dissected as a trigger.

Figure 11:
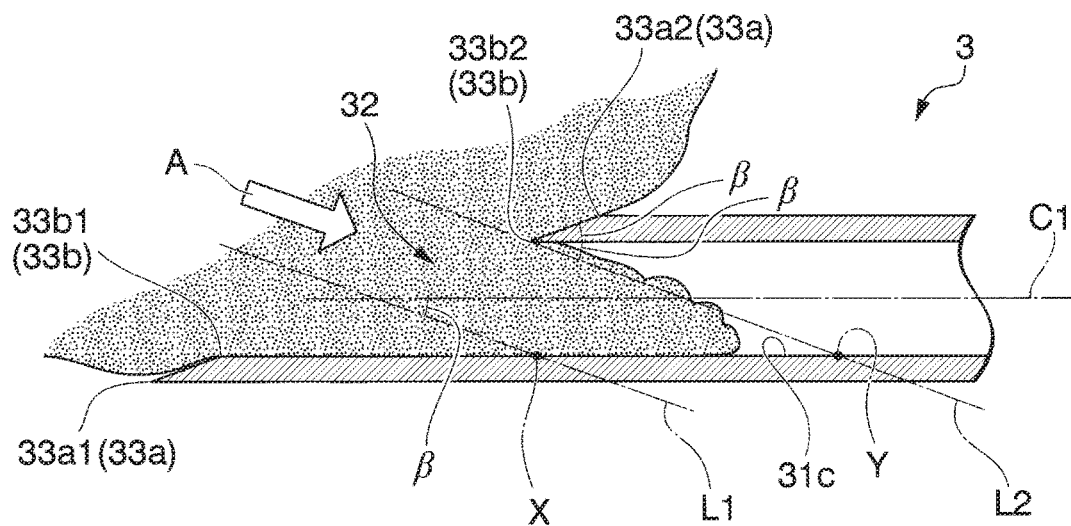
FIG. 11 is a schematic view showing a relation between tissue entering the needle tube of the biopsy needle and a side hole.
Figure 12:
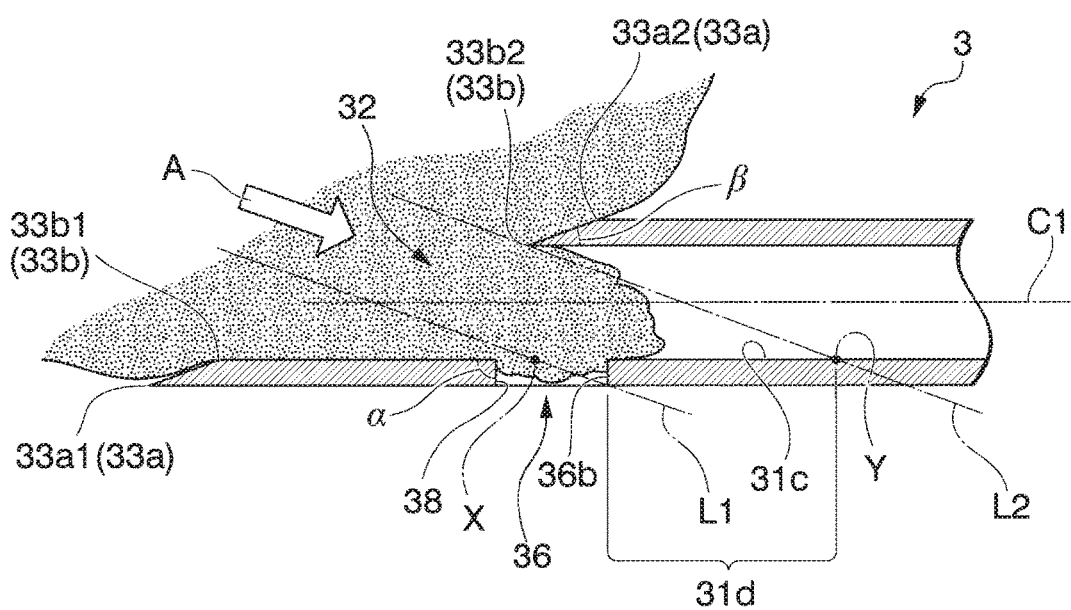
FIG. 12 is a schematic view showing the relation between the tissue entering the needle tube of the biopsy needle and the side hole.

FIG. 11 is a schematic view showing a relation between the tissue entering the needle tube 3 and the side hole 36. Further, in FIG. 11, the side hole 36 is omitted. FIG. 12 is a schematic view showing a relation between the tissue entering the needle tube 3 and the side hole 36.

As shown in FIG. 11, in a cross section passing through the central axis of the main body section 31 and the side hole 36 and parallel to the longitudinal axis, the distal opening section 32 is inclined to form an angle (β) with respect to the longitudinal axis of the main body section 31.

As shown in FIG. 11, in a cross section passing through the central axis of the main body section 31 and the side hole 36 and parallel to the longitudinal axis, a straight line (L1) passing through a middle point of a straight line connecting the bottommost end 33b2 and a foremost distal end 33b1 in the distal inner circumferential edge 33b of the distal opening section 32, extending in a proximal end direction from the middle point toward an inner circumferential surface at which the side hole 36 is formed, and having an angle β with respect to the longitudinal axis crosses the inner circumferential surface 31c at an intersection point (a position) X. In addition, a straight line (L2) passing through a position of the bottommost end 33b2 (the dissection blade section 35a) of the distal inner circumferential edge 33b and parallel to a straight line (L1) crosses the inner circumferential surface 31c at an intersection point (a position) Y. When the needle tube 3 is inserted in the tissue, the tissue torn by a proximal end 33b2 of the distal inner circumferential edge 33b enters the needle tube 3 in a direction of an arrow A (a direction extending at an angle β with respect to the inner circumferential surface 31c from the proximal end 33b2 of the distal inner circumferential edge 33b as an origin). The tissue entering the needle tube 3 is configured to press a region between the intersection point X and the intersection point Y in the inner circumferential surface 31c of the main body section 31 shown in FIG. 11.

For this reason, as shown in FIG. 12, the engaged surface 38 is disposed closer to the distal side than the intersection point (position) X, and an opposite surface opposite to the engaged surface 38 (the cross-sectional portion 36b) is disposed closer to the distal side than the intersection point (the position) Y. Accordingly, the tissue can easily enter from the distal opening section 32 of the needle tube 3, and the tissue is locked onto the engaged surface 38 to prevent the tissue from easily falling from the distal opening section 32 of the needle tube 3. Further, the incision blade section 39 is also formed in a region between the position X and the position Y.

Further, as shown in FIG. 12, the opposite surface (the cross-sectional portion 36b) is disposed closer to the distal side than the intersection point Y to become a receiving surface 31d configured not to exit the needle tube 3 (the main body section 31) again via the side hole 36 and to stop the tissue at the inner circumferential surface 31c of the main body section 31 when the tissue torn by the proximal end 33*b*2 of the distal inner circumferential edge 33*b* enters the needle tube 3 in the direction of the arrow A (a direction extending at the angle β with respect to the inner circumferential surface 31*c* using the proximal end 33*b*2 of the distal inner circumferential edge 33*b* as the origin). As the above-mentioned side hole 36 is formed, the biological tissue entering from the distal opening section 32 can easily enter the side hole 36 when the tissue is punctured, and according to an action of the receiving surface 31*d*, the tissue cannot easily exit from the side hole 36 to the outside of the needle tube 3 (the main body section) again. Further, the tissue is locked onto the engaged surface 38 when the needle tube 3 is removed from the tissue, and the tissue can more easily stay in the main body section 31.

As shown in FIGS. 8 and 9, the engaged surface 38 is disposed in the vicinity of a substantially opposite position with the centerline C1 of the main body section 31 sandwiched therebetween with respect to the bottommost end 33*b*2 (the dissection blade section 35*a*) disposed closest to the proximal end in the distal inner circumferential edge 33*b* of the distal opening section 32.

As shown in FIG. 5, the engaged surface 38 may be a plane substantially perpendicular to the centerline C1 of the main body section 31 to lock the tissue captured in the main body section 31 via the distal opening section 32, and is directed toward the proximal end 31*b* of the main body section 31. That is, the engaged surface 38 is directed to a side of the longitudinal axis of the main body section 31 opposite to a distal opening 33 of the distal opening section 32. In addition, the engaged surface 38 is disposed at an opposite position of the dissection blade section 35*a* serving as an end portion disposed closest to a proximal end of an inner circumferential portion 33*b* of the distal opening 33 of the distal opening section 32 with the centerline C1 of the main body section 31 interposed therebetween. That is, as shown in FIG. 9, the engaged surface 38 is disposed at an opposite position of a proximal end of the opening end 33*c* (a blade surface) of the distal opening section 32 (in the embodiment, a proximal end 33*b*2 of the inner circumferential portion 33*b* of the opening end 33*c*) with the centerline C1 of the main body section 31 interposed therebetween.

Further, as shown in FIGS. 7 and 10, the engaged surface 38 has an arc-shaped cross section of the main body section 31, a surface thereof is substantially planar, and the tissue captured in the main body section 31 via the distal opening section 32 can be easily locked.

Further, more preferably, the engaged surface 38 may be disposed within a range closer to the distal side than a bottommost end 33*a*2 of the distal outer circumferential edge 33*a* of the opening end 33*c* of the distal opening section 32 and closer to the proximal end side than the bottommost end 33*b*2 of the distal inner circumferential edge 33*b*.

In addition, even when the opening of the side hole 36 has a circular shape, while the engaged surface 38 is formed at the distal opening section 32 side in an edge of the opening, in this case, a surface of the engaged surface 38 is not a plane substantially perpendicular to the centerline C1 of the main body section 31 and is formed in a curved surface having a semi-circular portion of a circular shape or a part of the hemispherical portion.

The incision blade section 39 is a blade section disposed at a boundary portion between an inner surface of the main body section 31 and the engaged surface 38 along the inner circumference of the main body section 31 and capable of forming an incision by being caught by the tissue captured in the main body section 31 via the distal opening section 32. The incision blade section 39 may not be sharp, and, for example, in the embodiment, as the inner surface of the main body section 31 and the engaged surface 38 are connected at an angle of 90°, the incision capable of dissecting the tissue can be formed in the tissue. Note that, the incision blade section 39 may be sharp. Further, a third angle α formed by the engaged surface 38 (the cross-sectional portion 36*a*) and the inner circumferential surface 31*c* of the main body section 31 is formed to be larger than the above-mentioned second angle γ, and the third angle α is not limited to 90° but may be set to, for example, a range of 80 to 120°. Accordingly, a balance between ease of catching the tissue in the needle tube 3 on the engaged surface 38 and prevention of the tissue from falling from the side hole 36 of the needle tube 3 is achieved.

The cross-sectional portion 36*b* may be formed not to be easily caught on the tissue captured in the main body section 31 via the distal opening section 32. For example, the cross-sectional portion 36*b* may have a curved surface.

Corner portions in the cross-sectional portion 36*b* that continues to the inner surface of the main body section 31 may have tapered surfaces such that the tissue captured in the main body section 31 from the distal opening section 32 can more easily enter the proximal end 31*b* side of the main body section 31 beyond the side hole 36.

The proximal end opening section 41 is an opening into which the stylet 27 is inserted. In addition, the proximal end opening section 41 can also be used as an extracting port configured to collect a piece of tissue when the piece of tissue is captured in the main body section 31 of the needle tube 3.

The sheath 7 shown in FIG. 3 is a flexible tubular member formed of a resin tube, a metal strand coil, or the like, and both ends of which are open. The needle tube 3 is inserted through the sheath 7 to advance and retreat.

The manipulation section 8 shown in FIG. 3 includes a manipulation main body 9, a sheath adjuster 18 connected to the manipulation main body 9, and a needle slider 23 installed at a proximal end side of the manipulation main body 9.

The manipulation main body 9 has a lumen through which the needle tube 3 and the sheath 7 can be inserted. The sheath adjuster 18 is attached to the distal side of the manipulation main body 9. The proximal side of the manipulation main body 9 is inserted into the needle slider 23 formed in a tubular shape. The manipulation main body 9 and the sheath adjuster 18, and the manipulation main body 9 and the needle slider 23 can slide in an axial direction while relative rotation around the axis is suppressed because grooves, convex portions, and so on (not shown), formed at the outer circumferential surfaces thereof are engaged with each other.

The sheath adjuster 18 is connected to be movable with respect to the manipulation main body 9 to adjust a protrusion amount of the sheath 7 from the distal end of the channel 107 of the ultrasonic endoscope 100. A distal portion of the sheath adjuster 18 is detachably attached to the proximal port member 107*b* of the ultrasonic endoscope 100.

The needle slider 23 is fixed to the proximal end of the needle tube 3. In addition, the needle slider 23 is connected to the manipulation main body 9 to be movable with respect to the manipulation main body 9.

Since the proximal end side of the needle tube 3 protrudes from the proximal end of the sheath 7 to be fixed to the needle slider 23, as the needle slider 23 slides with respect to the manipulation main body 9, the needle tube 3 can protrude and retreat from the distal end of the sheath 7.

Movement of the needle slider 23 is restricted by the stopper 61 such that the needle slider 23 can advance to the manipulation main body 9 to only a position at which the needle slider 23 comes in contact with a stopper 61. As a fixed position of the stopper 61 with respect to the manipulation main body 9 is adjusted, a maximum protrusion length from the sheath 7 of the needle tube 3 can be adjusted.

A state in which the needle slider 23 is disposed at the proximal end side of the manipulation main body 9 to the position at which the needle slider 23 moves to a limit is an initial state before use of the biopsy needle 1. In the initial state, the distal end of the needle tube 3 is in the sheath 7.

The stylet 27 is attached to the proximal end portion of the needle slider 23. The stylet 27 is a needle-shaped member inserted through the needle tube 3. When the stylet 27 is removed from the proximal end portion of the needle slider 23, instead of the stylet 27, a suction means such as a syringe or the like can be attached to the proximal end portion of the needle slider 23.

Next, an action of the biopsy needle 1 will be described. FIGS. 13 to 16 are views showing an action of the needle tube 3 of the biopsy needle 1.

In use of the biopsy needle 1, the insertion body 2 of the biopsy needle 1 shown in FIG. 3 is inserted through the channel 107 of the ultrasonic endoscope 100 shown in FIG. 1, and the distal end of the insertion body 2 protrudes from the distal end of the channel 107. Next, after position adjustment of the sheath 7 using the sheath adjuster 18, an operator moves the needle slider 23 distally to cause the needle tube 3 to protrude from the distal end of the sheath 7.

Figure 13:
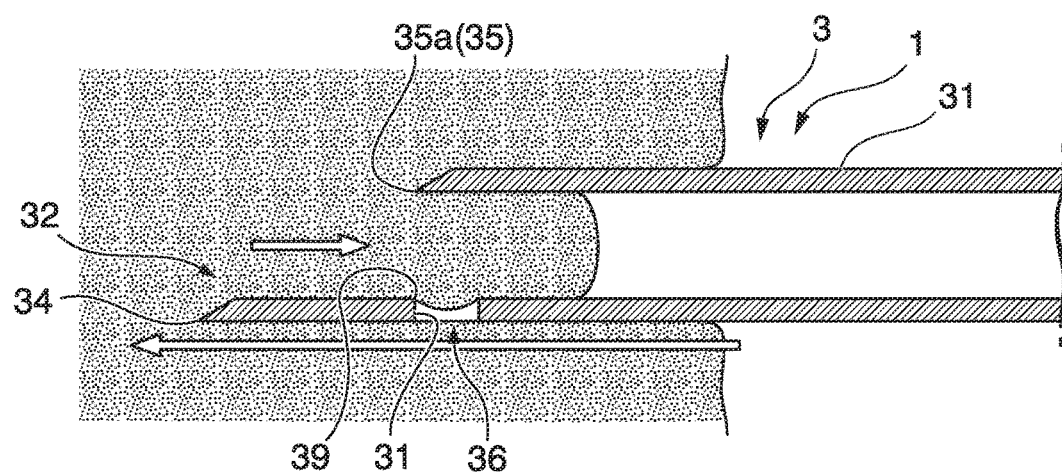
FIG. 13 is a view showing an action of the needle tube of the biopsy needle.
Figure 15:
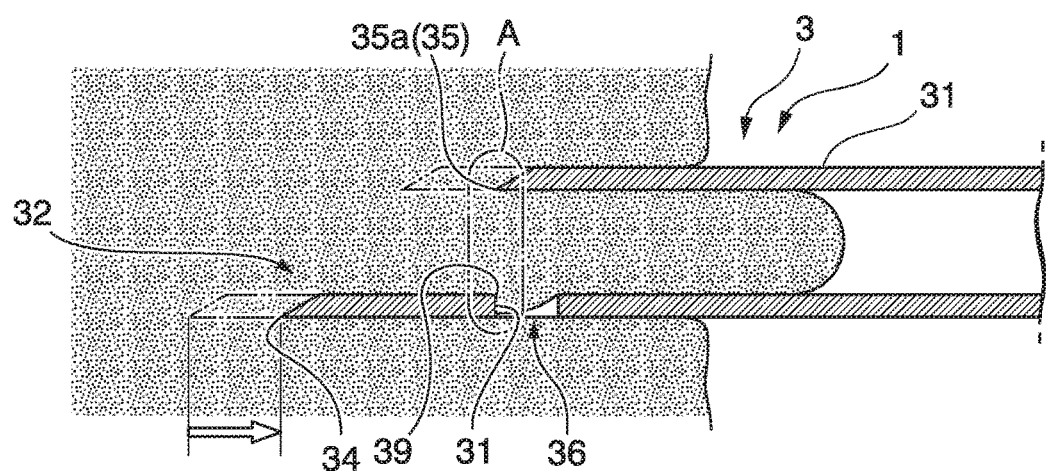
FIG. 15 is a view showing the action of the needle tube of the biopsy needle.

As shown in FIG. 13, a puncture blade section 34 formed at the distal opening section 32 of the needle tube 3 is pushed into an organ while dissecting the organ serving as the biopsy target. Further, after the needle tube 3 is inserted in the organ, as the stylet 27 (see FIG. 3) is pulled toward the proximal end or the stylet 27 is removed and a known suction tool such as a syringe or the like is attached to a proximal end portion of the needle slider 23, as shown in FIG. 15, the pressure inside of the main body section 31 of the needle tube 3 becomes negative.

Figure 14:
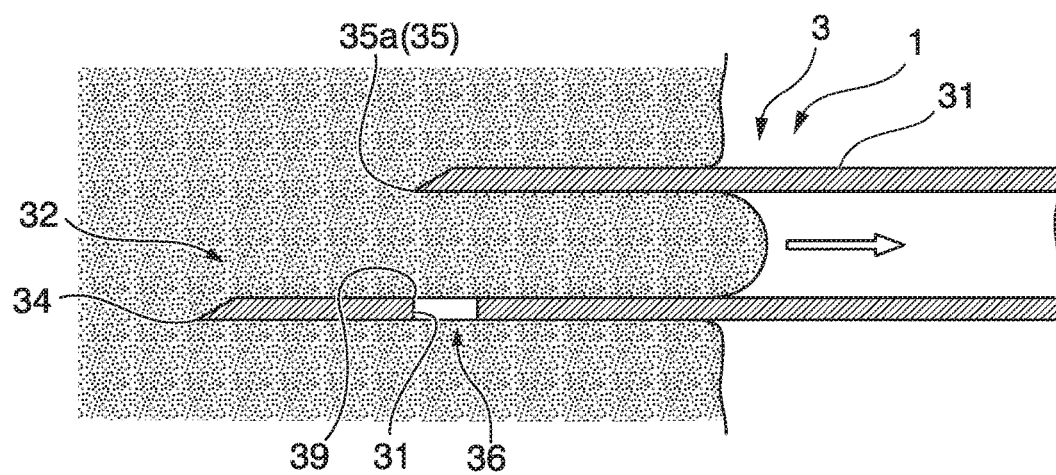
FIG. 14 is a view showing the action of the needle tube of the biopsy needle.

In a process in which the needle tube 3 is pushed into the organ as shown in FIGS. 13 and 14, the tissue directly enters the needle tube 3 from the distal opening section 32 toward the side hole 36, and in the vicinity of the proximal end of the distal inner circumferential edge 33*b* of the distal opening section 32, the tissue is dissected by the dissection blade section 35*a* such that the tissue of the organ is captured in the main body section 31. The piece of tissue dissected by the dissection blade section 35*a* and entering the main body section 31 from the distal opening section 32 is further pushed into the proximal end 31*b* (see FIG. 5) side of the main body section 31 beyond the side hole 36.

When a distal portion of the piece of tissue is not completely cut out of the biopsy target organ, if the needle tube 3 is pulled out of the organ, the piece of tissue is pulled in a direction from the distal opening section 32 of the needle tube 3 toward the outside of the needle tube 3. Here, as shown in FIG. 15, the piece of tissue disposed closer to the proximal end side in the main body section 31 than the engaged surface 38 of the side hole 36 is hooked to the side hole 36 when the piece of tissue abuts the engaged surface 38, and the piece of tissue is held in the main body section 31 of the needle tube 3 against a force causing it to be pulled out of the needle tube 3. Alternatively, in the process in which the tissue enters the needle tube 3, when the tissue enters the side hole 36 and the needle tube 3 is pulled out of the organ, the piece of tissue is locked to the engaged surface 38.

Further, the incision blade section 39 disposed at the boundary portion between the inner surface of the main body section 31 and the engaged surface 38 of the side hole 36 forms an incision in the piece of tissue by a force pulling the piece of tissue toward the distal side of the needle tube 3 in a state in which the piece of tissue abuts the engaged surface 38.

In the state in which the incision is formed by the incision blade section 39, the piece of tissue is torn off using the incision as a trigger. Further, since the tissue is dissected by the dissection blade section 35*a* in a proximal portion in the distal inner circumferential edge 33*b* of the distal opening section 32, a region between the incision with respect to the piece of tissue and the dissection portion by the dissection blade section 35*a* becomes a region A (see FIG. 15) in which the piece of tissue can be easily torn off.

Figure 16:
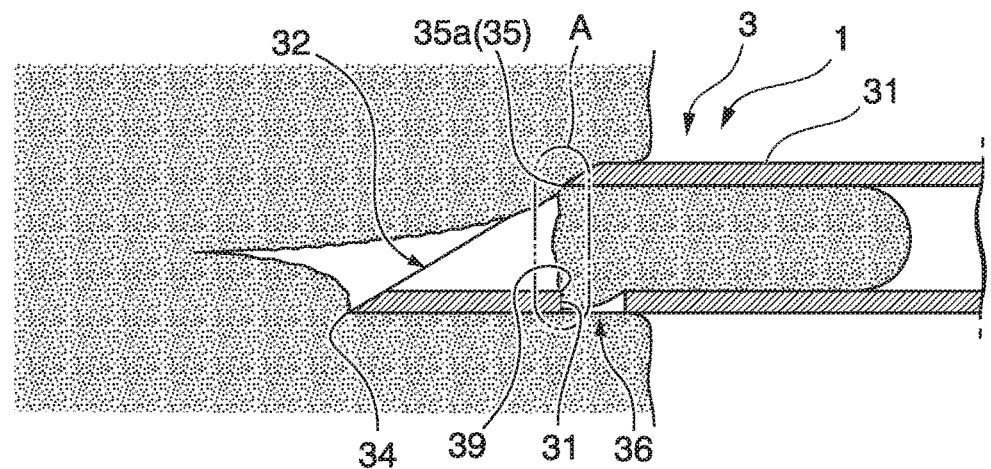
FIG. 16 is a view showing the action of the needle tube of the biopsy needle.

As the piece of tissue is disposed closer to the proximal end side than the side hole 36, the inside of the needle tube 3 is maintained in a negative pressure state at a position closer to the proximal end side of the needle tube 3 than the piece of tissue. Since the piece of tissue in the main body section 31 is pulled toward the proximal end 31*b* of the main body section 31 when the pressure inside of the main body section 31 of the needle tube 3 is negative, when the piece of tissue in the main body section 31 receives a pulling force toward the distal 31*a* side of the main body section 31 by manipulation in a direction in which the needle tube 3 is pulled out of the organ from the organ, as shown in FIG. 16, the piece of tissue is dissected such that the tissue is torn off at the above-mentioned region A at which the tissue can be most easily torn off. For this reason, the piece of tissue disposed closer to the proximal end side than the engaged surface 38 of the side hole 36 remains in the main body section 31 of the needle tube 3 and is dissected from the organ.

Accordingly, a sufficient amount of tissue required for diagnosis can be collected without repeating inserting-in and pulling-out operations of the needle tube 3 with respect to the organ a plurality of times. For this reason, the organ serving as the biopsy target is not excessively injured.

As described above, in the needle tube 3 of the biopsy needle 1 of the embodiment, the tissue captured once in the needle tube 3 is held in the main body section 31 of the needle tube 3 by the engaged surface 38 formed in the side hole 36 of the needle tube 3. For this reason, the piece of tissue cannot easily fall from the needle tube 3 of the embodiment.

In addition, since the side hole 36 is a through-hole, in comparison with the case in which the side hole 36 is a simple recess rather than the through-hole, the side hole 36 can be easily formed, and an area of the engaged surface 38 can be largely secured.

In addition, since an opening area of the through-hole of the side hole 36 is equal to or smaller than a cross-sectional area of the main body section 31 of the needle tube 3, the piece of tissue captured in the main body section 31 enters the proximal end 31*b* of the main body section 31 beyond the side hole 36 to be held without being discharged to the outside of the main body section 31 from the through-hole of the side hole 36.

In addition, the incision blade section 39 disposed at the boundary portion between the engaged surface 38 of the side hole 36 and the inner surface of the main body section 31 can generate the incision from which the piece of tissue is torn off in the piece of tissue in a state in which the piece of tissue is in the main body section 31 as a trigger.

In addition, since the engaged surface 38 and the incision blade section 39 are formed between the position X and the position Y that are described above, a cutting force can be securely transmitted to the tissue at a boundary between a position of the tissue surrounded by the inner circumferential surface 31c of the needle tube 3 and a position that is not surrounded thereby.

In addition, the piece of tissue captured in the main body section 31 of the needle tube 3 using the biopsy needle 1 of the embodiment has a substantially columnar shape defined by a shape of the distal opening section 32. For this reason, in the embodiment, injury of the piece of tissue that causes difficulty in pathological diagnosis performed by making a tissue section cannot easily occur. In addition, since the needle tube 3 of the biopsy needle 1 of the embodiment cuts off the organ in a substantially columnar shape and cells in the piece of tissue cannot be easily broken in the process of the biopsy, the piece of tissue captured in the main body section 31 of the needle tube 3 using the biopsy needle 1 of the embodiment is a sample appropriate for biochemical inspection using the piece of tissue.

(Variant 1)

Figure 17:
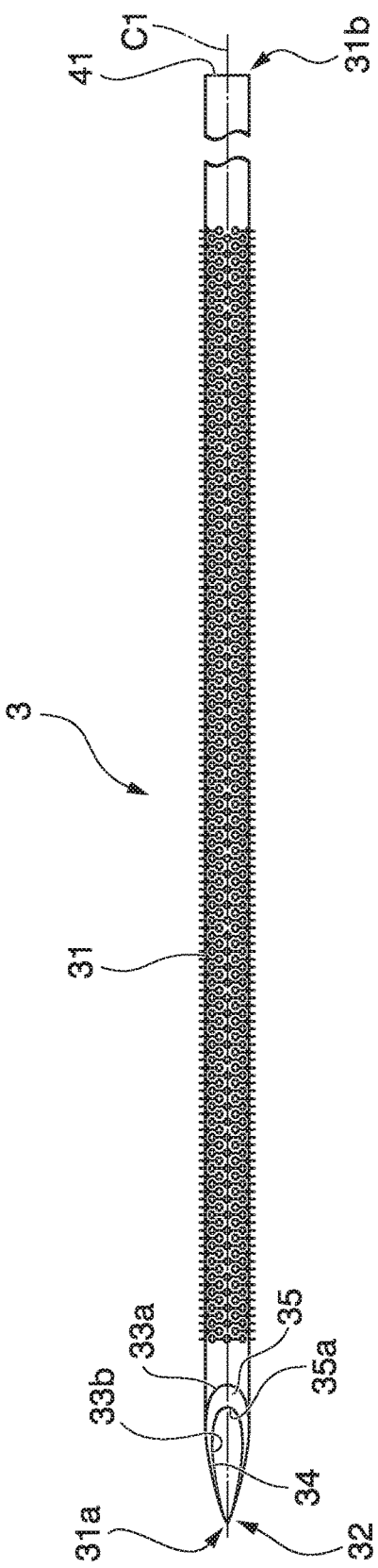
FIG. 17 is a plan view of a needle tube of a variant of the embodiment.
Figure 18:
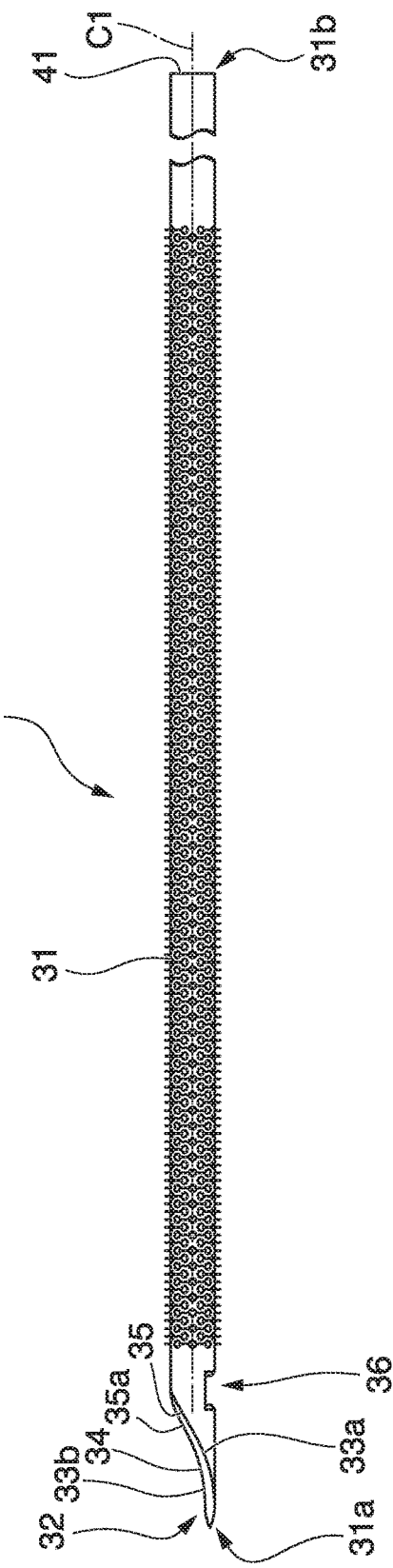
FIG. 18 is a side view of the needle tube of the variant of the embodiment.
Figure 19:
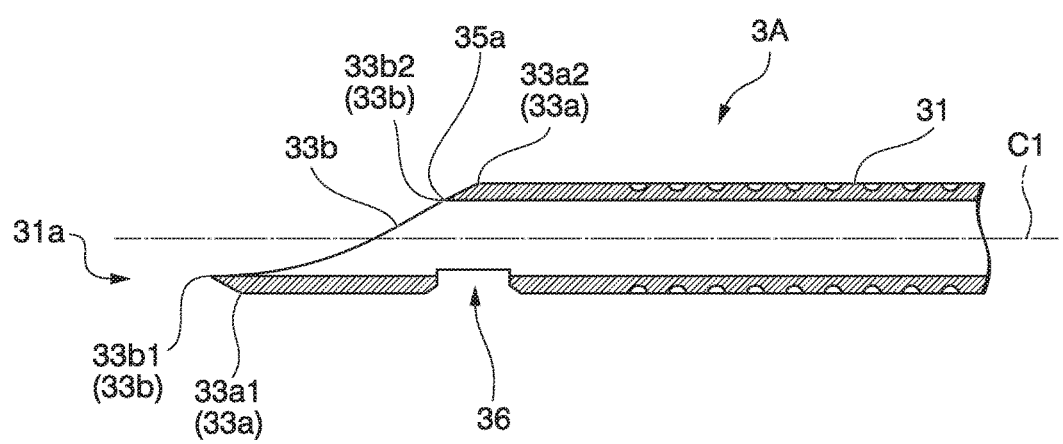
FIG. 19 is a cross-sectional view of a distal portion of the needle tube of the variant of the embodiment.

Next, a variant of the embodiment will be described. FIG. 17 is a plan view of a needle tube of the variant. FIG. 18 is a side view of the needle tube of the variant. FIG. 19 is a cross-sectional view of a distal portion of the needle tube of the variant.

As show in FIGS. 17 to 19, in the variant, instead of the needle tube 3 described in the embodiment, a needle tube 3A (a Menghini needle) is provided.

That is, in the embodiment, the puncture blade section 34 is formed throughout the circumference of the needle tube 3A along the distal inner circumferential edge 33b of the distal opening section 32 of the needle tube 3A. The needle tip is the foremost distal end 33b1 of the distal inner circumferential edge 33b. Further, in the variant, like the embodiment, the dissection blade section 35a is provided at the distal inner circumferential edge 33b of the distal opening section 32 of the needle tube 3A. In the variant, the puncture blade section 34 and the dissection blade section 35a are continuous, and are not clearly distinct.

The needle tube 3A of the variant has the side hole 36 described in the embodiment.

In the variant, when the needle tube 3A punctures the tissue, since the distal inner circumferential edge 33b of the distal opening section 32 of the needle tube 3A is a sharp blade as a whole, the tissue can be easily dissected in a substantially columnar shape by the puncture blade section 34. Since the needle tube 3A is a Menghini needle and a distal end thereof is sharp, the tissue is easily punctured. Further, since the needle tube 3A has an edge formed at a blade surface, the tissue can easily enter the main body section 31 through the distal opening section 32. The tissue entering the needle tube 3A cannot easily leak to the outside of the main body section 31 through the distal opening section 32 by an action of the engaged surface 38 of the side hole 36. Based on this, in the variant, since the tissue entering the main body section 31 cannot be easily discharged after the tissue is punctured and the ease with which the tissue is punctured and the tissue enters the main body section 31 upon insertion in the tissue are improved, a larger amount of tissue can be collected in comparison with another needle shape.

Hereinabove, while the embodiment of the present invention has been described in detail with reference to the accompanying drawings, specific configurations are not limited to the embodiment but may include design changes without departing from the spirit of the present invention.

For example, the shape of the needle tip in the distal opening section 32 of the needle tube may be different from the shape described in the embodiment and the variant thereof. Specifically, a shape that can be applied to a medical needle such as a lancet, a semi-lancet, a backcut, a trocar, a twin peak, a crown cut, or the like may be employed as the shape of the needle tip in the distal opening section 32 of the needle tube.

In addition, in the embodiment, while the side hole 36 disposed in the needle tube is exemplified as the through-hole, the side hole 36 having the engaged surface 38 of the piece of tissue may be opened in the needle tube or may not be opened in the outer surface of the needle tube.

In addition, the engaged surface 38 may be disposed at a position separated from a position opposite to the dissection blade section 35a in the circumferential direction of the main body section 31 with the centerline C1 of the main body section 31 interposed therebetween.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A needle tube comprising:
   a tubular main body section having a distal end, a proximal end, an inner circumferential surface and an outer circumferential surface, and having an internal space formed by the inner circumferential surface;
   a distal opening section formed at a distal end of the main body section to be inclined with respect to a longitudinal axis of the main body section, and to have a distal opening in communication with the internal space;
   a needle tip formed at a distal end of the distal opening section;
   a side hole disposed proximally to the needle tip and passing through the inner circumferential surface and the outer circumferential surface of the main body section;
   a side hole inner circumferential edge extending around the longitudinal axis of the main body section at a position at which the side hole and the inner circumferential surface of the main body section intersect;
   a side hole outer circumferential edge extending around the longitudinal axis of the main body section at a position at which the side hole and the outer circumferential surface of the main body section intersect;
   an engaged surface formed between the side hole inner circumferential edge and the side hole outer circumferential edge to be directed toward the proximal end of the main body section, the engaged surface being configured to engage biological tissue entering from the distal opening section,
   wherein the side hole forms an opening area smaller than that of the distal opening;
   a distal inner circumferential edge formed to intersect the distal opening section and the inner circumferential surface of the main body section;

a distal outer circumferential edge that continues from the distal opening section and the outer circumferential surface of the main body section; and a blade surface formed between the inner circumferential edge and the outer circumferential edge to surround the distal opening, wherein, in a cross section passing through a central axis of the main body section and the side hole and parallel to the longitudinal axis:

the distal opening section is inclined to form an angle (β) with respect to the longitudinal axis of the main body section;

a straight line (L1) extending in a proximal end direction from a center of the distal opening toward an inner circumferential surface of a side at which the side hole is formed and forming the angle (β) with respect to the longitudinal axis crosses an intersection point (X) with the inner circumferential surface; and the engaged surface is disposed distally to the intersection point (X).

2. The needle tube according to claim 1, wherein, in a cross section passing through a central axis of the main body section and the side hole and parallel to the longitudinal axis:

a straight line (L2) parallel to the straight line (L1) and passing through a proximal end of the distal inner circumferential edge crosses an intersection point (Y) with the inner circumferential surface; and an opposite surface which faces the engaged surface is disposed distally to the intersection point (Y).

3. The needle tube according to claim 2, wherein, in the cross section passing through a central axis of the main body section and the side hole and parallel to the central axis:

the engaged surface and the inner circumferential surface of the main body section form an angle (α);

in a proximal end of the distal inner circumferential edge, the blade surface and the inner circumferential surface of the main body section form the angle (β); and in a cross section passing through the side hole and perpendicular to the central axis, when at least one of an angle formed by a first cross-sectional portion, which extends along a central axis of the main body, of the side hole and the inner circumferential surface of the main body section and an angle formed by a second cross-sectional portion, which extends along the central axis of the main body, of the side hole and the inner circumferential surface of the main body section is an angle (γ), the angle (γ) is larger than the angle (β) and smaller than the angle (α).

4. The needle tube according to claim 1, wherein, in a cross section of the main body section perpendicular to a central axis of the main body section:

an opening width of the side hole inner circumferential edge is smaller than an inner diameter of the main body section; and an opening width of the side hole outer circumferential edge is larger than the inner diameter of the main body section.

5. The needle tube according to claim 1, wherein the engaged surface is disposed at an opposite position of a proximal end of the blade surface inclined with respect to a centerline of the main body section, with the centerline of the main body section interposed therebetween.

6. The needle tube according to claim 1, wherein the engaged surface is disposed at an opposite position of the proximal end of the distal inner circumferential edge, with the centerline of the main body section interposed therebetween.

7. The needle tube according to claim 1, wherein the distal opening section has a sharp puncture blade section that is configured to enable the main body section to puncture the tissue in an entire periphery of the distal end of the main body section.

8. The needle tube according to claim 2, wherein the opposite surface has a curved surface configured to prevent the biological tissue, which has entered from the distal opening section, from being caught on the opposite surface.

9. The needle tube according to claim 2, wherein the opposite surface includes a corner portion that continues to the inner circumferential surface of the main body section, and the corner portion has a tapered surface configured to facilitate entry of the biological tissue, which has entered from the distal opening section, into a distal end side of the main body section beyond the side hole.

10. A needle tube comprising:

a tubular main body section having a distal end, a proximal end, an inner circumferential surface and an outer circumferential surface, and having an internal space formed by the inner circumferential surface;

a distal opening section formed at a distal end of the main body section to be inclined with respect to a longitudinal axis of the main body section, and to have a distal opening in communication with the internal space;

a needle tip formed at a distal end of the distal opening section;

a side hole disposed proximally to the needle tip and passing through the inner circumferential surface and the outer circumferential surface of the main body section;

a side hole inner circumferential edge extending around the longitudinal axis of the main body section at a position at which the side hole and the inner circumferential surface of the main body section intersect;

a side hole outer circumferential edge extending around the longitudinal axis of the main body section at a position at which the side hole and the outer circumferential surface of the main body section intersect;

an engaged surface formed between the side hole inner circumferential edge and the side hole outer circumferential edge to be directed toward the proximal end of the main body section, the engaged surface being configured to engage biological tissue entering from the distal opening section, wherein the side hole forms an opening area smaller than that of the distal opening;

a distal inner circumferential edge formed to intersect the distal opening section and the inner circumferential surface of the main body section;

a distal outer circumferential edge that continues from the distal opening section and the outer circumferential surface of the main body section; and a blade surface formed between the inner circumferential edge and the outer circumferential edge to surround the distal opening, wherein in a cross section passing through a central axis of the main body section and the side hole and parallel to the longitudinal axis, the distal opening section is inclined to form an angle (β) with respect to the longitudinal axis of the main body section, a straight line (L1) extending in a proximal end direction from a center of the distal opening toward an inner circumferential surface of a side at which the side hole is formed and forming the angle (β) with respect to the longitudinal axis crosses an intersection point (X) with the inner circumferential surface, a straight line (L2) parallel to the straight line (L1) and passing through a proximal end of the distal inner circumferential edge crosses an intersection point (Y) with the inner circumferential surface, and an opposite surface which faces the engaged surface is disposed distally to the intersection point (Y).

11. The needle tube according to claim 10, wherein, in the cross section passing through a central axis of the main body section and the side hole and parallel to the central axis, the engaged surface and the inner circumferential surface of the main body section form an angle (α), in a proximal end of the distal inner circumferential edge, the blade surface and the inner circumferential surface of the main body section form the angle (β), and in a cross section passing through the side hole and perpendicular to the central axis, when at least one of an angle formed by a first cross-sectional portion, which extend along a central axis of the main body, of the side hole and the inner circumferential surface of the main body section and an angle formed by a second cross-sectional portion, which extend along the central axis of the main body, of the side hole and the inner circumferential surface of the main body section is an angle (γ), and the angle (γ) is larger than the angle (β) and smaller than the angle (α).

12. The needle tube according to claim 10, wherein, in a cross section of the main body section perpendicular to a central axis of the main body section, an opening width of the side hole inner circumferential edge is smaller than an inner diameter of the main body section, and an opening width of the side hole outer circumferential edge is larger than the inner diameter of the main body section.

13. The needle tube according to claim 10, wherein the side hole further has an incision blade section disposed at a boundary portion between the inner circumferential surface of the main body section and the engaged surface along an inner circumference of the main body section and configured to dissect tissue captured in the main body section.

14. The needle tube according to claim 10, wherein the engaged surface is disposed at an opposite position of a proximal end of the blade surface inclined with respect to a centerline of the main body section, with the centerline of the main body section interposed therebetween.

15. The needle tube according to claim 10, wherein the engaged surface is disposed at an opposite position of the proximal end of the distal inner circumferential edge, with the centerline of the main body section interposed therebetween.

16. The needle tube according to claim 10, wherein the engaged surface is a plane with respect to the inner circumferential surface of the main body section.

17. The needle tube according to claim 10, wherein the distal opening section has a sharp puncture blade section that is configured to enable the main body section to puncture the tissue in an entire periphery of the distal end of the main body section.

18. The needle tube according to claim 10, wherein the opposite surface has a curved surface configured to prevent the biological tissue, which has entered from the distal opening section, from being caught on the opposite surface.

19. The needle tube according to claim 10, wherein the opposite surface includes a corner portion that continues to the inner circumferential surface of the main body section, and the corner portion has a tapered surface configured to facilitate entry of the biological tissue, which has entered from the distal opening section, into a distal end side of the main body section beyond the side hole.

20. A biopsy system comprising:

an endoscope; and a needle tube which is configured to connect with the endoscope, the needle tube including:

a tubular main body section having a distal end, a proximal end, an inner circumferential surface and an outer circumferential surface, and having an internal space formed by the inner circumferential surface;

a distal opening section formed at a distal end of the main body section to be inclined with respect to a longitudinal axis of the main body section, and to have a distal opening in communication with the internal space;

a needle tip formed at a distal end of the distal opening section;

a side hole disposed proximally to the needle tip and passing through the inner circumferential surface and the outer circumferential surface of the main body section;

a side hole inner circumferential edge extending around the longitudinal axis of the main body section at a position at which the side hole and the inner circumferential surface of the main body section intersect;

a side hole outer circumferential edge extending around the longitudinal axis of the main body section at a position at which the side hole and the outer circumferential surface of the main body section intersect; and an engaged surface formed between the side hole inner circumferential edge and the side hole outer circumferential edge to be directed toward the proximal end of the main body section, the engaged surface being configured to engage biological tissue entering from the distal opening section, wherein the side hole forms an opening area smaller than that of the distal opening, and wherein in a cross section passing through a central axis of the main body section and the side hole and parallel to the longitudinal axis, the distal opening section is inclined to form an angle (β) with respect to the longitudinal axis of the main body section, a straight line (L1) extending in a proximal end direction from a center of the distal opening toward an inner circumferential surface of a side at which the side hole is formed and forming the angle (β) with respect to the longitudinal axis crosses an intersection point (X) with the inner circumferential surface, a straight line (L2) parallel to the straight line (L1) and passing through a proximal end of the distal inner circumferential edge crosses an intersection point (Y) with the inner circumferential surface, and an opposite surface which faces the engaged surface is disposed distally to the intersection point (Y).

* * * * *